US012780769B2

(12) United States Patent
Blight et al.

(10) Patent No.: US 12,780,769 B2
(45) Date of Patent: Nov. 3, 2026

(54) PROCESS FOR THE RECOVERY OF ETHANOL FROM CRUDE ETHYL ACETATE

(71) Applicant: JOHNSON MATTHEY DAVY TECHNOLOGIES LIMITED, London (GB)

(72) Inventors: Richard James Blight, London (GB); Ian Campbell, London (GB); Brendan Michael Hannan, London (GB); Joseph Tohill, Stockton-on-Tees (GB)

(73) Assignee: Johnson Matthey Davy Technologies Limited, London (GB)

( * ) Notice: Subject to any disclaimer, the term of this patent is extended or adjusted under 35 U.S.C. 154(b) by 98 days.

(21) Appl. No.: 18/861,777

(22) PCT Filed: Jun. 14, 2023

(86) PCT No.: PCT/GB2023/051550
§ 371 (c)(1),
(2) Date: Oct. 30, 2024

(87) PCT Pub. No.: WO2023/242566
PCT Pub. Date: Dec. 21, 2023

(65) Prior Publication Data
US 2025/0304515 A1 Oct. 2, 2025

(30) Foreign Application Priority Data
Jun. 16, 2022 (GB) ..................................... 2208864

(51) Int. Cl.
*C07C 29/82* (2006.01)

(52) U.S. Cl.
CPC .................................... *C07C 29/82* (2013.01)

(58) Field of Classification Search
CPC ........... C07C 29/80; C07C 29/82; C07C 7/06; C07C 31/08
See application file for complete search history.

(56) References Cited

U.S. PATENT DOCUMENTS 4,372,822 A * 2/1983 Muller .................... C07C 29/80 203/25
4,448,644 A * 5/1984 Foster ..................... C07C 29/82 203/DIG. 19

(Continued)

FOREIGN PATENT DOCUMENTS

WO 00/20374 A1 4/2000
WO 00/20375 A1 4/2000

(Continued)

*Primary Examiner* — Jonathan Miller
(74) *Attorney, Agent, or Firm* — BakerHostetler

(57) ABSTRACT

A process for the recovery of substantially dry ethanol from a feedstock comprising ethyl acetate, ethanol and water, said process comprising: (a) passing said feedstock to a first separation column which includes a first separation column reboiler, and is maintained under distillation conditions to form an intermediate bottom stream comprising ethanol and water and having a higher ethanol concentration than the ethanol concentration in said feedstock; (b) passing said intermediate bottom stream to an azeotrope column maintained under distillation conditions to form an azeotrope column bottom stream, and an azeotrope column overhead stream which comprises ethanol and water; (c) feeding an ethanol make-up stream into said azeotrope column; (d) passing said azeotrope column overhead stream through a water removal section for separating water from ethanol to form a substantially dry ethanol stream; (e) using said substantially dry ethanol stream to provide heat in said first separation column reboiler.

11 Claims, 3 Drawing Sheets

(56) References Cited

U.S. PATENT DOCUMENTS

| | | | | | |
|---|---|---|---|---|---|
| 4,636,284 | A * | 1/1987 | English | B01D 3/40 | 203/84 |
| 5,124,004 | A * | 6/1992 | Grethlein | B01D 3/007 | 203/50 |
| 5,294,304 | A * | 3/1994 | Kano | C07C 29/84 | 568/918 |
| 7,297,236 | B1 * | 11/2007 | Vander Griend | B01D 3/005 | 202/205 |
| 7,553,397 | B1 * | 6/2009 | Colley | C07C 67/54 | 203/14 |
| 8,541,633 | B2 * | 9/2013 | Horton | C07C 29/152 | 568/885 |
| 8,552,226 | B2 * | 10/2013 | Powell | B01D 3/143 | 568/885 |
| 8,802,903 | B2 * | 8/2014 | Weiner | C07C 29/149 | 568/885 |
| 9,975,828 | B2 * | 5/2018 | Bailey | C07C 29/149 | |
| 12,497,345 | B2 * | 12/2025 | Toth | B01D 3/143 | |
| 2011/0190550 | A1 * | 8/2011 | Horton | C07C 29/152 | 568/885 |
| 2011/0190552 | A1 * | 8/2011 | Powell | C07C 29/149 | 568/885 |
| 2013/0116480 | A1 * | 5/2013 | Johnston | C07C 29/80 | 568/885 |
| 2013/0245334 | A1 * | 9/2013 | Weiner | C07C 29/149 | 568/885 |
| 2014/0058139 | A1 | 2/2014 | Powell | | |
| 2017/0190644 | A1 * | 7/2017 | Bailey | C07C 67/08 | |

FOREIGN PATENT DOCUMENTS

| | | | |
|---|---|---|---|
| WO | 0020373 | W | 4/2000 |
| WO | 2011097208 | A2 | 8/2011 |
| WO | 2011097214 | A2 | 8/2011 |

* cited by examiner

PROCESS FOR THE RECOVERY OF ETHANOL FROM CRUDE ETHYL ACETATE

FIELD OF THE INVENTION

The present invention relates to a process for the recovery of substantially dry ethanol from a feedstock comprising ethyl acetate, ethanol and water.

BACKGROUND

Commercial processes for the production of ethyl acetate employ dehydrogenation of ethanol via acetaldehyde to ethyl acetate in the vapour phase over a copper based heterogeneous catalyst. Residual aldehydes and ketones in the crude ethyl acetate product, some of which would be difficult to remove from the product by distillation, are selectively hydrogenated back to alcohols in a liquid phase polishing reactor. Two column pressure swing distillation is then used to separate unreacted ethanol and water from the ethyl acetate in the crude product stream, with a final column to remove heavies from the ethyl acetate product. An example of such a process is disclosed in WO 00/20373, WO 00/20374 and WO 00/20375.

The pressure swing distillation system requires two columns, a first low-pressure separation column and a second higher pressure separation column. The first separation column is maintained under distillation conditions to form a bottom stream comprising ethanol and water and an overhead stream comprising light components such as diethyl ether, methanol, ethane and gases such as hydrogen, methane and carbon dioxide. In the arrangement disclosed in WO 00/20373, WO 00/20374 and WO 00/20375, a side draw which comprises ethyl acetate, ethanol and water is taken from the first separation column and fed to the second separation column. The second separation column is maintained under distillation conditions to form a bottom stream comprising high purity ethyl acetate and an overhead stream comprising ethyl acetate, ethanol and water which is returned to the first separation column above the feed point of the crude product stream. Both the first and the second separation columns in the pressure swing distillation system require reboilers.

The unreacted ethanol, water and by-products in the bottom stream from the first separation column in the pressure swing distillation system are then recycled to another column, known as an azeotrope column. Here, fresh wet ethanol feed is added and the overheads, which largely comprise ethanol, are sent to a drying package to remove water down to a low level. The dried ethanol from the drying package is then used in the feed to the dehydrogenation reactor.

It is desirable to optimise energy inputs into this process, especially in view of the need to minimise energy use and incorporate renewable energy as we transition to a low to zero carbon economy.

SUMMARY OF THE INVENTION

Accordingly, the present invention provides a process for the recovery of substantially dry ethanol from a feedstock comprising ethyl acetate, ethanol and water, said process comprising:

(a) passing said feedstock to a first separation column which includes a first separation column reboiler, and is maintained under distillation conditions to form an intermediate bottom stream comprising ethanol and water and having a higher ethanol concentration than the ethanol concentration in said feedstock;

(b) passing said intermediate bottom stream to an azeotrope column maintained under distillation conditions to form an azeotrope column bottom stream, and an azeotrope column overhead stream which comprises ethanol and water and has a higher ethanol concentration than the ethanol concentration in said intermediate bottom stream;

(c) feeding an ethanol make-up stream into said azeotrope column;

(d) passing said azeotrope column overhead stream through a water removal section for separating water from ethanol to form a substantially dry ethanol stream;

(e) using said substantially dry ethanol stream to provide heat in said first separation column reboiler.

The inventors have surprisingly found that the substantially dry ethanol stream which exits the water removal package (the azeotrope column in combination with the water removal section) can be used to supplement, or completely replace, the external heat input required for the first separation column reboiler. This additional heat integration adds to the overall energy efficiency of a process for forming ethyl acetate by the dehydrogenation of ethanol and has benefit both in terms of cost and the minimised energy consumption because less steam needs to be raised, so less fuel is consumed in the boiler. Water consumption is also minimised, for example because less water coolant is required to condense the substantially dry ethanol stream.

Also provided is a process for the production of ethyl acetate by the dehydrogenation of ethanol, the process comprising the process of the invention for the recovery of substantially dry ethanol from a feedstock comprising ethyl acetate, ethanol and water.

DETAILED DESCRIPTION OF THE INVENTION

Figure 1:
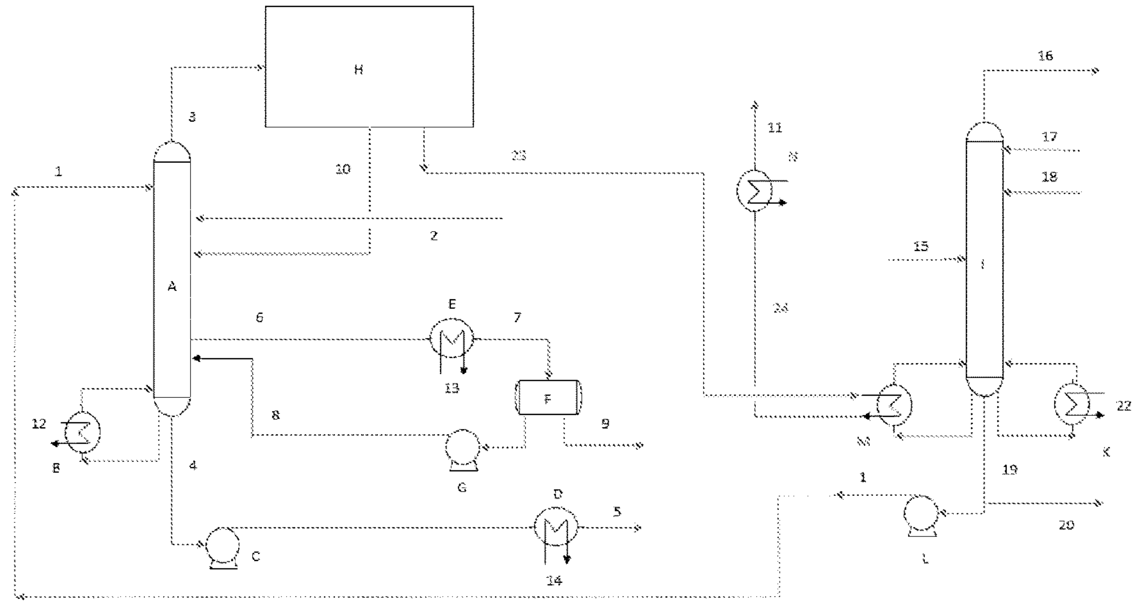
FIG. 1 is a schematic diagram of a process of the invention.

The feedstock may be a crude product stream recovered from the production of ethyl acetate by the dehydrogenation of ethanol and should be free from compounds whose presence in the feedstock would cause separation problems if the feedstock were to be directly refined. For example because their boiling points are close to that of ethyl acetate and because ethyl acetate tends to form distillates or azeotropes with such compounds. Such compounds include acetaldehyde, n-butyraldehyde and butan-2-one. Generally, these compounds are removed from the feedstock by selective hydrogenation, also known as polishing, using a suitable selective hydrogenation catalyst, for example as described in WO 00/20375. Accordingly, the feedstock will generally be substantially free of aldehydes and ketones. For example, the feedstock will contain less than about 0.01 wt % aldehydes and ketones. Therefore, the present process for the production of ethyl acetate by the dehydrogenation of ethanol will typically also comprise a polishing step of selective hydrogenation prior to the process of the invention for the recovery of substantially dry ethanol.

The feedstock will typically contain about 10 wt % or less water, and preferably about 5 wt % or less water. In addition to ethyl acetate, ethanol and water, the stream typically also contains light and heavy components. By the term "light" components is meant components that have lower boiling points than ethyl acetate and its azeotropes with water and ethanol. By the term "heavy" components is meant components with higher boiling points than ethanol and ethyl acetate.

The first separation column is maintained under distillation conditions to form an intermediate bottom stream comprising ethanol and water and having a higher ethanol concentration than the ethanol concentration in the feedstock. Also, an overhead stream comprising light components such as diethyl ether, methanol, ethane and gases such as hydrogen, methane and carbon dioxide is formed. A side draw which comprises ethyl acetate, ethanol and water may be taken from the first separation column and fed to a second separation column as part of a pressure swing distillation system for recovering substantially pure ethyl acetate, for example as disclosed in WO 00/20373. Alternatively, the overhead stream may be partially condensed then sent to a lights column where the light components are vented to a flare or a fuel header. The majority of the lights column bottom stream is then returned to the first separation column as reflux and the rest is fed to the second separation column. The first separation column is generally operated at a pressure of less that about 4 bara, preferably from about 1 bara to about 2 bara.

The intermediate bottom stream comprising ethanol and water formed in the first separation column will generally also contain any heavy components e.g. by-product organic components such as butanols and butyl acetates. The intermediate bottom stream will generally contain about 2.0 wt % or less water, and preferably about 1.0 wt % or less water. Typically, the intermediate product stream will contain at least about 0.5 wt % water. The intermediate bottom stream will generally contain at least about 80 wt % ethanol, and preferably at least about 90 wt % ethanol.

The azeotrope column is so called because it provides an overhead stream comprising ethanol and water which is typically at the ethanol/water azeotropic composition. The azeotrope column may contain any suitable internals, such as packing or trays. A skilled person can determine what packing to use and, for example, how many trays are required which may be determined, for example, by the concentration of water passing through the column. The azeotrope column rejects water and heavy components, which are generally present in the intermediate bottom stream in a higher concentration than is preferable for when ethanol is recycled back to a dehydrogenation reactor in a process for the production of ethyl acetate by the dehydrogenation of ethanol.

The azeotrope column will generally be operated with an overhead pressure of at least about 4.0 bara. The azeotrope column will generally be operated with an overhead pressure of about 5.0 bara or less. For example, about 4.6 bara.

Since ethanol and water form an azeotrope, it is not possible to remove all of the water from the azeotrope column overhead stream using the azeotrope column alone. Generally, the azeotrope column overhead stream has a water content of about 2.0 to about 6.0 wt %. To remove water from this stream, it is passed through a water removal section, which preferably comprises a molecular sieve, for separating water from ethanol to form a substantially dry ethanol stream which will be in the vapour phase. A 3 Å zeolite molecular sieve is typically used. Water molecules have a diameter of 2.5 Å, while ethanol molecules have a diameter of 4 Å, so 3 Å zeolites retain water, but reject ethanol. Alternatively, the water removal section may comprise a membrane system for separating water from ethanol. In such a membrane system, any residual water content would be a function of the surface area of the membrane. A hydrophilic membrane may be used, which would preferentially allow water through leaving ethanol concentrated on the high-pressure side. Some ethanol may pass through the membrane with the water, and that ethanol is returned to the azeotrope column. The substantially dry ethanol stream generally contains about 1.0 wt % or less water, typically about 0.5 wt % or less water, preferably about 0.05 wt % or less water.

Generally, the azeotrope column overhead stream is superheated by a temperature of at least about 15° C. Generally, the stream is superheated to a temperature of about 50° C. or less, for example about 20° C. This superheating step is to take the stream away from the dew point before it is passed to the water removal section. A molecular sieve selectively absorbs water over ethanol based on the size of the pores in the molecular sieve. Eventually, the water capacity of the molecular sieve is used up, such that feeding more azeotrope column overhead stream would result in breakthrough of water into the substantially dry ethanol stream. Since this is not desirable, the azeotrope column overhead stream may be diverted to another empty bed of molecular sieve whilst the bed saturated with water is put into regeneration. Regeneration removes water from the pores of the molecular sieve by back flowing dry ethanol through it and reducing the pressure in the bed to pull the water molecules out. Vacuum conditions may be used to maximise the removal of water. The liquid removed by the regeneration procedure is a mixture of water and ethanol, with a water concentration higher than the ethanol/water azeotrope. This, the aqueous regeneration stream, is collected and may be returned to the azeotrope column at a constant rate to a point below the feed. The returned water passes down the azeotrope column and is ultimately removed as aqueous effluent from the azeotrope column bottom stream. Typically, the aqueous regeneration stream is condensed under vacuum and so it would be difficult to recover any heat from it as the saturation temperature would be too low to be useful. As such it is generally cooled, typically to about 40° C., using cooling water. The aqueous regeneration stream may be re-heated before returning it to the azeotrope column. Advantageously, when the feedstock is a crude product stream recovered from the production of ethyl acetate by the dehydrogenation of ethanol heat exchange may be provided between the dehydrogenation reactor effluent and the aqueous regeneration stream. This heat exchange advantageously reduces any increased heat duty required on the azeotrope column to provide the substantially dry ethanol stream with the optimal temperature approach to the first separation column reboiler. In a typical ethyl acetate production flowsheet, this effluent stream passes through three interchangers to preheat other streams in the process. In a specific example, such an effluent stream will have a temperature of about 105° C., and can heat the aqueous regeneration stream from about 40° C. to typically about 95° C. Accordingly, the process of the invention may further comprise a step of regenerating the water removal section, preferably comprising a molecular sieve, thus providing an aqueous regeneration stream with a water concentration higher than the ethanol/water azeotrope and returning the aqueous regeneration stream to the azeotrope column. In the process for producing ethyl acetate, the effluent from the dehydrogenation reactor used to generate the feedstock is used to heat the aqueous regeneration stream before it is returned to the azeotrope column.

The dew point of the substantially dry ethanol stream is typically at least about 115° C. It is typically about 125° C. or less. The temperature approach between the dew point of the substantially dry ethanol stream and the temperature of the first separation column bottom stream is typically at least about 15° C., Generally, the temperature approach is about 25° C. or less, typically about 20° C. or less. By "temperature approach" means the smallest difference between the temperatures of the cold (reboiler) and hot (dew point of the substantially dry ethanol) streams. A skilled person will understand that the dew point is the temperature at which a superheated vapour begins to condense at a specific pressure; it may also be referred to as the saturation temperature.

Advantageously, such a temperature approach means that the latent heat from condensation of the substantially dry ethanol stream can be used to provide heat in the first separation column reboiler, which typically has a sump temperature of about 95° C. to about 100° C., typically about 99° C. to about 100° C., using a heat transfer area for the reboiler which is possible in real world use. The normal consumption of low-pressure steam in the first separation column reboiler is thus no longer required, reducing consumption of steam and the fuel to raise it from a boiler. When the temperature approach is not sufficiently large, it is not possible to produce an economic design for the first separation column reboiler due to the very large heat transfer area which would be required. Surprisingly, the additional heat requirement to increase the overhead pressure in the azeotrope column and raise the dew point of the substantially dry ethanol stream does not negate the advantage of reduced steam and fuel requirement afforded by the heat exchange of the invention. The first separation column may comprise a supplemental steam reboiler which may be required, for example, during start-up of the process.

The ethanol make-up stream accounts for ethanol that has been converted into ethyl acetate and by-products in an upstream dehydrogenation process and ensures that there is balance of ethanol mass between the feed to an ethanol dehydrogenation reactor and the first separation column. Generally, the ethanol make-up stream contains about 10.0 wt % or less water, typically about 5.0 wt % or less water, for example 2.5 wt % or less water.

A condensed ethanol stream, which may be partially or fully condensed, is produced in the first separation column reboiler from the substantially dry ethanol stream. The condensed ethanol stream typically leaves the reboiler at a temperature of from about 110° C. to about 130° C., or to about 120° C. Heat integration may be provided between the condensed ethanol stream and the ethanol make-up stream which is generally fed from a storage tank at ambient temperature, typically about 25° C. Accordingly, the condensed ethanol stream formed in the first separation column reboiler is used to provide heat to the ethanol make-up stream before it is fed into the azeotrope column. This completes the condensation of the substantially dry ethanol stream, if necessary, and advantageously counteracts any increased heat duty required in the azeotrope column reboiler to provide the substantially dry ethanol stream with the optimal temperature approach to the first separation column reboiler.

Heavy components introduced into the azeotrope column via the intermediate bottom stream can be at least partially removed by recovering a liquid side draw comprising water and organics from near the bottom of the azeotrope column. The liquid side draw typically comprises less than about 4.0 wt % ethanol, preferably less than about 0.1 wt % ethanol to give advantageous phase separation. Typically, the liquid side draw is recovered from near the bottom of the azeotrope column, cooled by passing through a cooler, then passed to a decanter, wherein the decanter provides an aqueous stream having a higher water concentration than the liquid side draw, and an organic stream having a higher organics concentration than the liquid side draw, wherein the aqueous stream is returned into the azeotrope column. The removal of heavy components using the azeotrope column decanter allows them to be purged without the loss of ethanol, thus improving the feed efficiency of an ethyl acetate production process in which the present process is integrated. Generally, the aqueous stream contains at least about 90 wt % water and the organics stream contains 20 wt % or less water. Generally, the liquid side draw is cooled to a temperature of from about 30° C. to about 50° C., for example about 40° C. Cooling the liquid side draw causes the water and organics to become immiscible and form separate phases of different densities which can be separated using weirs and baffle plates. When the cooled side draw is left to settle in the decanter vessel two liquid phases form, with a dense aqueous phase at the bottom and a less dense organic phase sitting on top of it. This separation allows reduction of the contained oxygen demand of the aqueous effluent from the bottom of the azeotrope column and allow the organics to be recovered for use as a fuel without free water.

Heat integration may be provided between the liquid side draw and the aqueous stream that is returned from the decanter into the azeotrope column. Accordingly, prior to or instead of passing through the cooler, the liquid side draw may be used to heat the aqueous stream before the aqueous stream is returned to the azeotrope column. This heat exchange advantageously reduces any increased heat duty required on the azeotrope column to provide the substantially dry ethanol stream with the optimal temperature approach to the first separation column reboiler.

Heat integration may also be provided between the azeotrope column bottom stream and the aqueous stream before the aqueous stream is returned to the azeotrope column. Accordingly, the azeotrope column bottom stream may be used to heat the aqueous stream before the aqueous stream is returned to the azeotrope column. This heat exchange also advantageously reduces any increased heat duty required on the azeotrope column to provide a substantially dry ethanol stream with the optimal temperature approach to the first separation column reboiler.

In some arrangements, there may from time to time be brief interruptions in the substantially dry ethanol stream from the water removal section. For example, if molecular sieves are used in the water removal section, a molecular sieve arrangement may comprise two or more beds of molecular sieve and, as described above, when the water capacity of a first molecular sieve bed is used up, flow may be diverted to another molecular sieve bed while the first molecular sieve bed is regenerated. Regenerating a molecular sieve bed typically involves reducing the pressure and then back-flowing fluid through the bed. When the regenerated bed is brought back online it needs to be repressurised. If the bed is back flowed and/or repressurized using the substantially dry ethanol stream, this will cause a significant reduction in the flow of the substantially dry ethanol stream to the first separation column reboiler for a period. The backflow typically uses a lower flowrate for a longer period and the re-pressurisation a higher flowrate for a shorter period. Preferably therefore, there is provided a quick start reboiler on the first separation column in addition to the first separation column reboiler. The quick start reboiler is preferably a reboiler that can be started up in less than 10 minutes, preferably less than 5 minutes and more preferably less than 1 minute. The quick start reboiler is preferably an electric reboiler. It will be appreciated that a regular steam reboiler may take time to heat up and may not therefore be suitable for circumstances where heat is needed for a short period of time. The quick start reboiler, preferably the electric reboiler, may be used to provide heat during reductions or interruptions of flow of the substantially dry ethanol stream to the first separation column reboiler. Alternatively or additionally, provision may be made for a further source of ethanol, typically ethanol vapour, to be fed to the water removal section at times when there is an increased demand for ethanol in the water removal section, for example during re-pressurisation, or backflow, of a part of the water removal section such as a molecular sieve bed. In that way, the flow rate of the substantially dry ethanol stream to the first separation column reboiler could be maintained even when extra ethanol, typically ethanol vapour, is required in the water removal section. The further source of ethanol is preferably the ethanol make-up stream. Thus, the ethanol make-up stream may be further connected to the water removal section, preferably via a vaporiser, most preferably an electric vaporiser, so that ethanol from the ethanol make-up stream can also be supplied to the water removal section. It will be appreciated that supply of ethanol from the ethanol make-up stream to the water removal section may be additional to, and not instead of, the feeding of the ethanol make-up stream to the azeotrope column. The increased amount of ethanol make-up required is not problematic, since the ethanol make-up stream is typically drawn from a storage tank and therefore and increased supply is possible during periods when ethanol from the ethanol make-up stream is also being supplied to the water removal section.

The present invention will now be described, by way of example, with reference to the accompanying figures. It will be understood by those skilled in the art that the drawings are diagrammatic and that further items of equipment such as reflux drums, pumps, vacuum pumps, compressors, gas recycle compressors, temperature sensors, pressure relief valves, control valves, flow controllers, level controllers, and the like may be required in a commercial plant. The provision of such ancillary items of equipment forms no part of the present invention and is in accordance with conventional chemical engineering practice.

As shown in FIG. 1 a feedstock comprising ethyl acetate, ethanol and water is fed in line 15 to first separation column I. The feedstock is from the polishing hydrogenation step after the dehydrogenation of ethanol over a copper based heterogeneous catalyst. This part of the process is not shown. The feedstock will also comprise light components such as diethyl ether, methanol, ethane and gases such as hydrogen, methane and carbon dioxide and heavy components such as butanols and butyl acetates. The feedstock will generally contain liquid and vapour phase components, the composition of which is dependent on upstream conditions and not critical to the present process.

The first separation column I includes a reboiler M. Substantially dry ethanol stream 23 which is in the vapour phase is used to provide heat to reboiler M. This replaces a steam reboiler present in conventional processes and offers the advantages discussed herein. The ethanol stream 24 leaving reboiler M is then cooled in ethanol condensate cooler N and can be fed back into an ethanol dehydrogenation process. A gas reboiler K may also be present in which heat from a vapour stream 22 produced in another part of the ethyl acetate production process may be utilised, such as the high-pressure second separation column in a pressure swing distillation system.

An intermediate bottom stream 19 is recovered from the bottom of first separation column I and passed through pump L before being fed as stream 1 into azeotrope column A at or near the top of the azeotrope column. After a period of operation, a purge of, for example, up to 1.5 wt % of intermediate bottom stream 19 may be taken in stream 20 to stop accumulation of unwanted by-products. An overhead stream 16 comprising light components such as diethyl ether, methanol and ethane is formed. Stream 16 is partially condensed then sent to a lights column (not shown) where the light components are vented to a flare or a fuel header. The majority of the lights column bottom stream is returned to the first separation column as reflux in stream 17, the rest is fed to a high-pressure second separation column (not shown) as part of a pressure swing distillation system. Stream 18 is the condensed overhead stream from the second separation column which is at the high-pressure azeotrope composition, so depleted in ethyl acetate relative to stream 16.

Azeotrope column A is operated at an overhead pressure of about 4.6 bara, resulting in an azeotrope column overhead stream 3 at a temperature of about 123° C. The azeotrope column overhead stream 3 contains ethanol and water, with a water content of about 2.2 wt % to about 5.5 wt %. This stream is then superheated by about 20° C. and passed to molecular sieve package H, which removes water from the stream. The substantially dry ethanol stream 23 leaves the molecular sieve package with a temperature of about 122° C. and a slightly reduced pressure. This temperature means that the latent heat from condensation of the substantially dry ethanol stream can advantageously be used to provide reboil heat to the bottom of the first separation column via reboiler M, which has a sump temperature of about 99° C. The normal consumption of low-pressure steam to the first separation column is thus no longer required, reducing consumption of steam and the fuel to raise it from a boiler. The azeotrope column uses a reboiler B heated with steam 12, which provides the extra heat duty imposed on the azeotrope column by the higher operating pressure. Surprisingly, the additional heat requirement here does not negate the advantage of reduced heat and steam consumption provided by the heat exchange of the invention.

An aqueous regeneration stream 10 containing removed water produced during regeneration of the molecular sieve, is returned to the azeotrope column at a constant rate to a point below the feed point of stream 1. A bottom stream 4 containing predominantly water is recovered from the bottom of the azeotrope column A through pump C, cooled in bottoms cooler D with water coolant stream 14 and discarded as aqueous effluent.

Ethanol make-up stream 2 is fed into the azeotrope column A near the top (below the top tray in the case trays are used) from a storage tank (not shown) at ambient temperature. The stream contains water, which is why it is optimal in the ethanol dehydrogenation process to add it to the system at this stage. The water in the make-up stream could otherwise facilitate deactivation of the ethanol dehydrogenation catalyst.

A liquid side draw 6 is recovered from near the bottom of the azeotrope column. This side draw contains water and organic heavy components, which are separated in decanter F after cooling of the side draw in cooler E with water coolant stream 13. The decanter contains baffle plates and weirs to remove the two phases separately and provide the aqueous stream 8 to be returned to the azeotrope column A via pump G. The organic phase is discarded as an organic purge stream 9.

Figure 2:
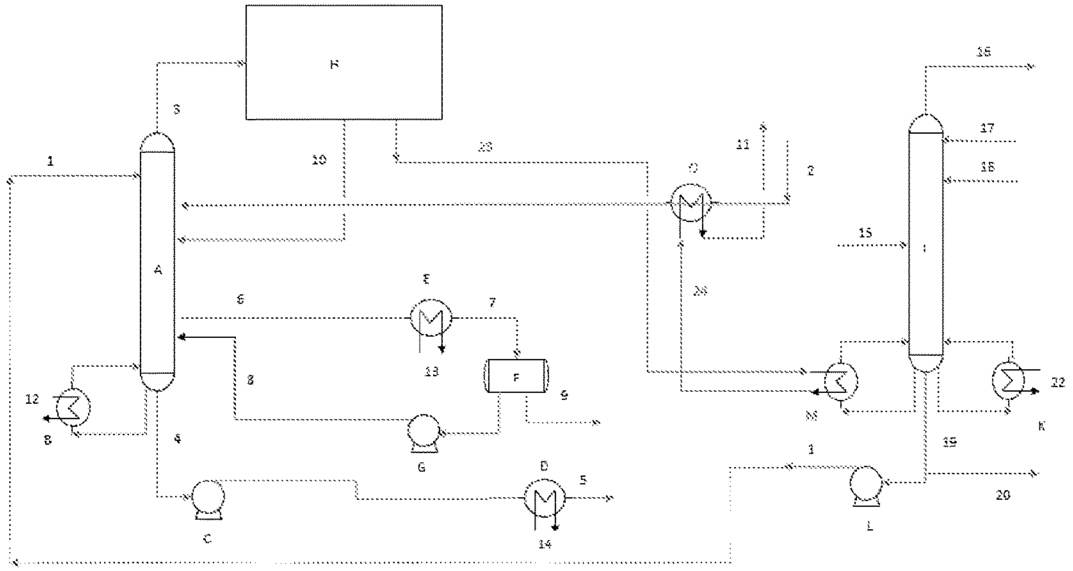
FIG. 2 is a schematic diagram of an additional aspect of the invention.

In the arrangement shown in FIG. 2, there is heat integration between the substantially dry ethanol stream after it has left first separation column reboiler M, and ethanol make-up feed 2. In this arrangement, heat is provided by stream 24 to ethanol make-up stream 2 in interchanger O. By heating the ethanol make-up stream the sensible heating required by the azeotrope column reboiler B is reduced, reducing its steam consumption. This also completes the condensation of the vapour phase substantially dry ethanol stream, if necessary, to provide stream 11.

Figure 3:
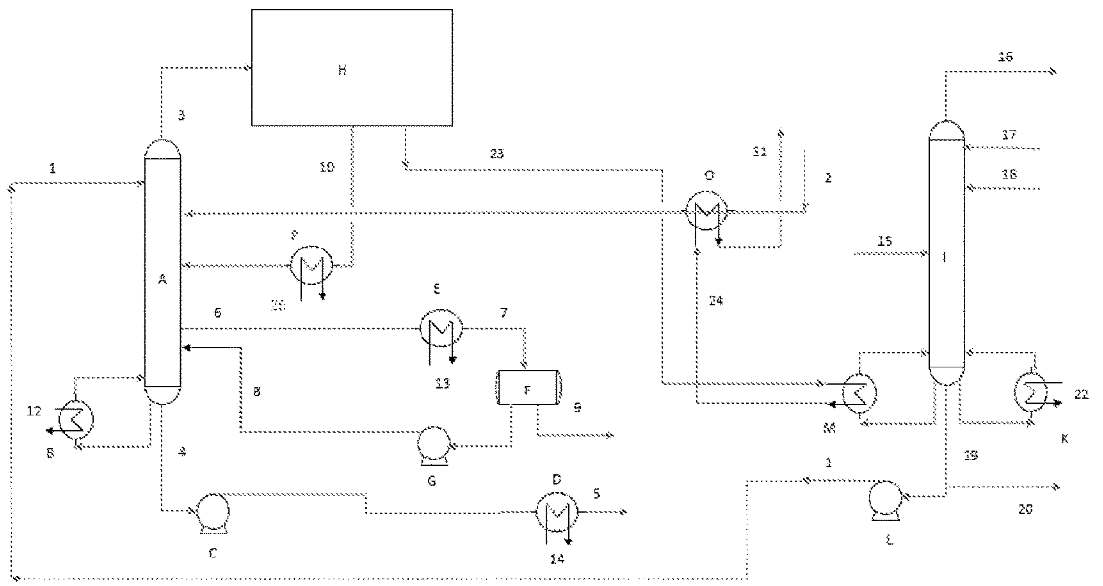
FIG. 3 is a schematic diagram of an additional aspect of the invention.

In the arrangement shown in FIG. 3, there is also heat integration between an aqueous regeneration stream 10 from regeneration of molecular sieve in water removal section H with a stream 26 which is an effluent stream from an upstream ethanol dehydrogenation reactor. In this arrangement, heat is provided by stream 26 to stream 10 in interchanger P. For regeneration, azeotrope column overhead stream 3 is diverted to an empty bed of molecular sieve whilst the bed saturated with water is put into regeneration by back flowing dry ethanol through it and reducing the pressure in the bed to pull the water molecules out. In a conventional ethyl acetate production process, the dehydrogenation effluent stream will have a temperature of about 105° C. It is condensing and has a substantially larger flowrate than the aqueous regeneration stream from the molecular sieve, so can heat that stream from, for example, from 40° C. to about 95° C. By heating the aqueous stream 26, the sensible heating required by the azeotrope column reboiler B is reduced, reducing its steam consumption via stream 12.

Figure 4:
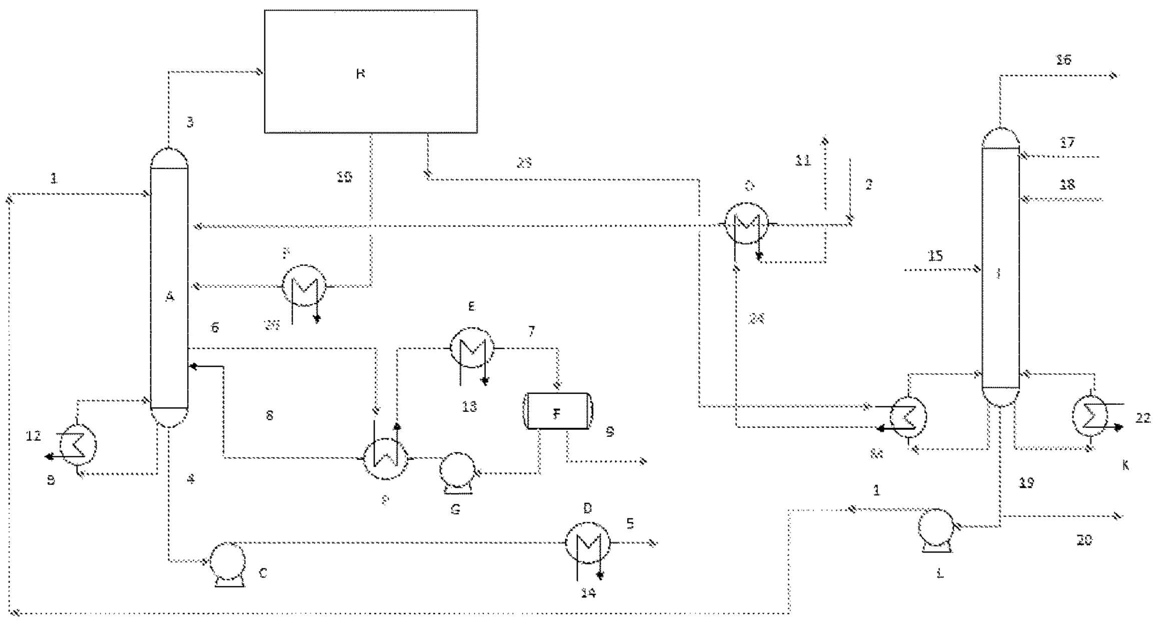
FIG. 4 is a schematic diagram of an additional aspect of the invention.

In the arrangement shown in FIG. 4, there is also heat integration between liquid side draw 6 and aqueous stream 8 being returned to azeotrope column A after the organics purge in decanter F. In this arrangement, prior to or instead of passing through cooler E, liquid side draw 6 is used to heat aqueous stream 8 in interchanger P. This arrangement can be advantageous when the ethanol make-up stream contains a low concentration of water because the flow of the azeotrope column bottom stream 4 may not be large enough to make interchange with the aqueous stream 8, as shown in FIG. 5, viable.

Figure 5:
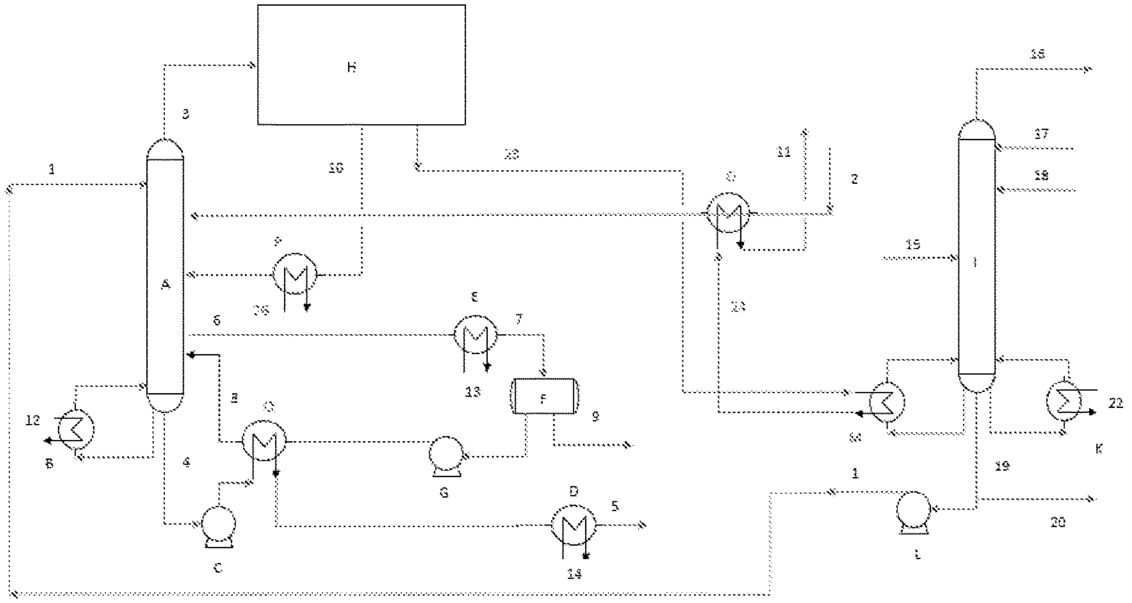
FIG. 5 is a schematic diagram of an additional aspect of the invention.

The arrangement shown in FIG. 5 is an alternative to the arrangement shown in FIG. 4, in which there is heat integration between the azeotrope column bottom stream 4 and the aqueous stream 8 being returned to azeotrope column A. In this arrangement, heat is provided by stream 4 to aqueous stream 8 in interchanger Q. By heating the aqueous stream 8, the sensible heating required by the azeotrope column reboiler B is reduced, reducing its steam consumption.

Figure 6:
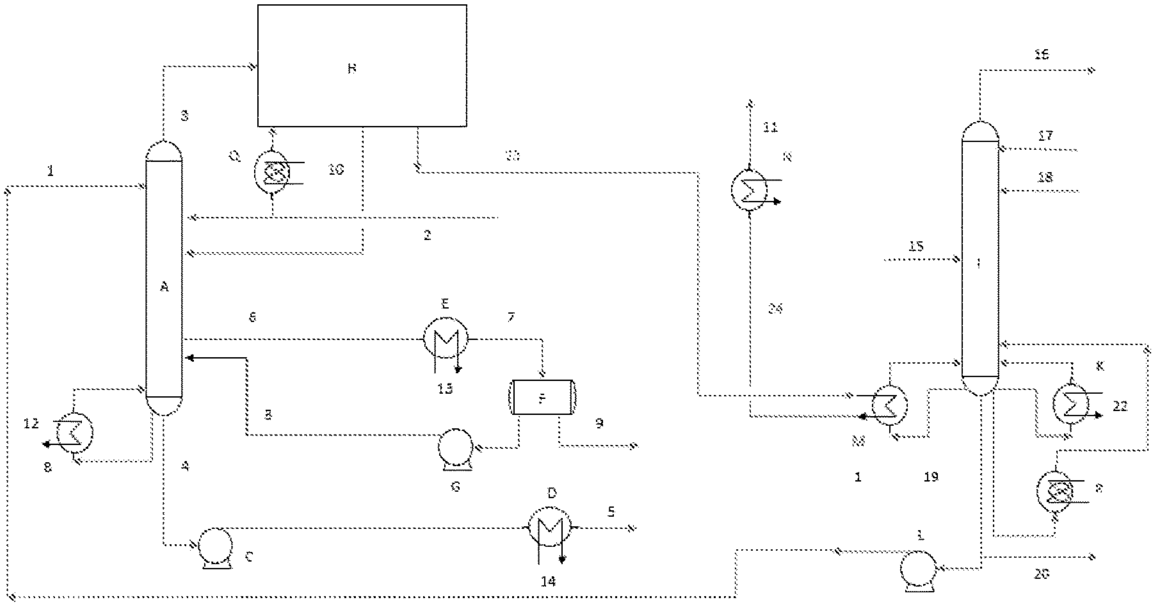
FIG. 6 is a schematic diagram of an additional aspect of the invention.

The arrangement shown in FIG. 6 is an alternative to the arrangement shown in FIG. 1. The arrangement includes a quick start reboiler, in the form of an electric reboiler R, on the first separation column I. The arrangement also includes electric vaporiser Q, through which ethanol from ethanol make-up stream 2 can be supplied to water removal section H. It will be appreciated that each of electric reboiler R and electric vaporiser Q can be present or not independently of one another in any particular embodiment and that electric reboiler R and/or electric vaporiser Q may be included alone or together in any of the arrangements of FIG. 1 to FIG. 5.

EXAMPLES

The exemplified processes form part of a flowsheet for the production of ethyl acetate by the dehydrogenation of ethanol and as such the feedstock for the processes is a crude product stream recovered from the production of ethyl acetate by the dehydrogenation of ethanol which has undergone a polishing hydrogenation.

The columns are simulated using AVEVA Pro/II Alcohols Package version 10.2.3.

Example 1

The following example demonstrates the advantages associated with heat exchange between the substantially dry ethanol stream and the first separation column reboiler.

In this example, a comparative process is run in which the azeotrope column pressure is a conventional 2.75 bara overhead and the heat exchange step of the invention is not included because it is not viable. Also, a process of the invention is run (in accordance with FIG. 1) in which the azeotrope column pressure is 4.6 bara overhead. This increases the pressure of the substantially dry ethanol vapours which exit the molecular sieve package, increasing the dew point from 103° C. to 121° C., and allows the temperature approach between the dew point of the substantially dry ethanol vapours and the sump of the first separation column to be increased from 6.8° C. to 24.8° C. As can be seen in Table 1, there is a net steam saving of between 0.62 and 0.63 MWh/Te EA evident across various ethanol make-up stream water concentrations. This surprisingly occurs despite an increase in the duty required for the azeotrope column reboiler.

TABLE 1

| Water content in ethanol make-up stream wt % | Increase in azeotrope column reboiler duty MWh/Te EA | First separation column reboiler saving MWh/Te EA | Net steam saving MWh/Te EA |
|---|---|---|---|
| 10 | 0.065 | 0.691 | 0.626 |
| 7.6 | 0.073 | 0.690 | 0.616 |
| 5 | 0.072 | 0.689 | 0.616 |
| 2 | 0.073 | 0.688 | 0.615 |
| 0.3 | 0.070 | 0.687 | 0.617 |

Example 2

The following example demonstrates that the increase in azeotrope column reboiler duty required can be offset by additional heat integrations, thus maximising the benefits of the invention.

In this example, the process of the invention is run with additional heat exchange between the substantially dry ethanol stream which has left the first separation column reboiler, and the ethanol make-up stream which is drawn from a storage tank at ambient temperature (in accordance with FIG. 2). As can be seen in Table 2, there is a net steam saving increase to between 0.70 and 0.71 MWh/Te EA evident across various ethanol make-up stream water concentrations.

TABLE 2

| Water content in ethanol make-up stream wt % | Increase in azeotrope column reboiler duty MWh/Te EA | First separation column reboiler saving MWh/Te EA | Net steam saving MWh/Te EA |
|---|---|---|---|
| 10 | −0.008 | 0.692 | 0.700 |
| 7.6 | −0.013 | 0.690 | 0.703 |
| 5 | −0.018 | 0.689 | 0.707 |
| 2 | −0.023 | 0.688 | 0.710 |
| 0.3 | −0.023 | 0.687 | 0.710 |

Example 3

The following example demonstrates that the increase in azeotrope column reboiler duty required can be further offset by additional heat integrations, thus maximising the benefits of the invention.

In this example, a process according to Example 2 is run, with additional heat exchange between an aqueous regeneration stream from the molecular sieve in the water removal section, and the effluent stream from an ethanol dehydrogenation rector (in accordance with FIG. 3). As can be seen in Table 3, there is a net steam saving increase to between 0.74 and 0.84 MWh/Te EA evident across various ethanol make-up stream water concentrations.

TABLE 3

| Water content in ethanol make-up stream wt % | Increase in azeotrope column reboiler duty MWh/Te EA | First separation column reboiler saving MWh/Te EA | Net steam saving MWh/Te EA |
|---|---|---|---|
| 10 | −0.150 | 0.691 | 0.841 |
| 7.6 | −0.063 | 0.690 | 0.753 |
| 5 | −0.060 | 0.689 | 0.748 |
| 2 | −0.054 | 0.688 | 0.742 |
| 0.3 | −0.050 | 0.687 | 0.737 |

Example 4

The following example demonstrates that the increase in azeotrope column reboiler duty required can be further offset by additional heat integrations, thus maximising the benefits of the invention.

In this example, a process according to Example 3 is run with additional heat exchange between a liquid side draw taken from near the bottom of the azeotrope column, and the aqueous stream being returned to the azeotrope column after separation from organics in a decanter (in accordance with FIG. 4). As can be seen in Table 4, there is a net steam saving increase to between 0.74 and 0.86 MWh/Te EA evident across various ethanol make-up stream water concentrations.

TABLE 4

| Water content in ethanol make-up stream wt % | Increase in azeotrope column reboiler duty MWh/Te EA | First separation column reboiler saving MWh/Te EA | Net steam saving MWh/Te EA |
|---|---|---|---|
| 10 | −0.170 | 0.689 | 0.859 |
| 7.6 | −0.079 | 0.690 | 0.769 |
| 5 | −0.069 | 0.689 | 0.758 |
| 2 | −0.062 | 0.688 | 0.750 |
| 0.3 | −0.054 | 0.687 | 0.742 |

The invention claimed is:

1. A method for producing ethyl acetate, the method comprising (i) producing ethyl acetate by dehydrogenation of ethanol, (ii) recovering a crude product stream, the crude product stream comprising ethyl acetate, ethanol, and water, and, (iii) feeding the crude product stream as a feedstock to a process for the recovery of substantially dry ethanol from the feedstock, said process comprising:

(a) passing said feedstock to a first separation column which includes a first separation column reboiler, and is maintained under distillation conditions to form an intermediate bottom stream comprising ethanol and water and having a higher ethanol concentration than the ethanol concentration in said feedstock;

(b) passing said intermediate bottom stream to an azeotrope column maintained under distillation conditions to form an azeotrope column bottom stream, and an azeotrope column overhead stream which comprises ethanol and water and has a higher ethanol concentration than the ethanol concentration in said intermediate bottom stream;

(c) feeding an ethanol make-up stream into said azeotrope column;

(d) passing said azeotrope column overhead stream through a water removal section for separating water from ethanol to form a substantially dry ethanol stream;

(e) using said substantially dry ethanol stream to provide heat in said first separation column reboiler, and, (f) using the substantially dry ethanol stream in a feed for the dehydrogenation of ethanol for producing the ethyl acetate.

2. The process of claim 1, wherein said azeotrope column is operated with an overhead pressure of at least about 4.0 bara.

3. The process of claim 1, wherein the dew point of said substantially dry ethanol stream is at least about 115° C.

4. The process of claim 1, wherein the temperature approach between the dew point of said substantially dry ethanol stream and the temperature of said first separation column bottom stream is at least about 15° C.

5. The process of claim 1, wherein said ethanol make-up stream contains about 10.0 wt % or less water.

6. The process of claim 1, wherein a condensed ethanol stream formed in said first separation column reboiler is used to provide heat to said ethanol make-up stream before said ethanol make-up stream is fed into said azeotrope column.

7. The process of claim 1, wherein a liquid side draw comprising water and organics is recovered from near the bottom of said azeotrope column, cooled by passing through a cooler, then passed to a decanter, wherein said decanter provides an aqueous stream having a higher water concentration than said liquid side draw, and an organic stream having a higher organics concentration than said liquid side draw, wherein said aqueous stream is returned to said azeotrope column.

8. The process of claim 7, wherein, prior to or instead of passing through said cooler, said liquid side draw is used to heat said aqueous stream before said aqueous stream is returned to said azeotrope column.

9. The process of claim 7, wherein said azeotrope column bottom stream is used to heat said aqueous stream before said aqueous stream is returned to said azeotrope column.

10. The process of claim 1, wherein said feedstock is substantially free of aldehydes and ketones.

11. The process of claim 1, further comprising a step of regenerating said water removal section thus providing an aqueous regeneration stream with a water concentration higher than the ethanol/water azeotrope and returning said aqueous regeneration stream to said azeotrope column, wherein effluent from an ethanol dehydrogenation reactor used to generate said feedstock is used to heat said aqueous regeneration stream before it is returned to said azeotrope column.

* * * * *